United States Patent
Osumi et al.

(10) Patent No.: US 8,202,221 B2
(45) Date of Patent: Jun. 19, 2012

(54) ULTRASONIC DIAGNOSTIC APPARATUS, ULTRASONIC IMAGE PROCESSING APPARATUS, AND ULTRASONIC IMAGE PROCESSING METHOD

(75) Inventors: Ryota Osumi, Nasushiobara (JP); Takeshi Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 641 days.

(21) Appl. No.: 12/338,447

(22) Filed: Dec. 18, 2008

(65) Prior Publication Data
US 2009/0171208 A1 Jul. 2, 2009

(30) Foreign Application Priority Data
Dec. 27, 2007 (JP) ................................. 2007-338276

(51) Int. Cl.
*A61B 8/00* (2006.01)
*G06K 9/00* (2006.01)
(52) U.S. Cl. ...................................... 600/443; 382/128
(58) Field of Classification Search .................. 600/437; 382/107, 128, 190, 203, 276
See application file for complete search history.

(56) References Cited

U.S. PATENT DOCUMENTS
2006/0084869 A1 4/2006 Kim et al.

FOREIGN PATENT DOCUMENTS
JP 2005-296331 10/2005
JP 2006-116307 5/2006

OTHER PUBLICATIONS

Khaled Z. Abd-Elmoniem et al., "Real-Time Speckle Reduction and Coherence Enhancement in Ultrasound Imaging via Nonlinear Anisotropic Diffusion", IEEE Transactions on Biomedical Engineering, vol. 49, No. 9, Sep. 2002, pp. 997-1014.
Office Action issued Apr. 20, 2011, in China Patent Application No. 200810190693.X (with English translation).
Yuan Xiugui Wang Chen, "An Anisotropic Diffusion Method for Image Noise Removal Based on Wavelet Transform", Mathematical Theory and Applications, vol. 27, No. 1, Mar. 2007, pp. 121-124.

*Primary Examiner* — Michael Rozanski
(74) *Attorney, Agent, or Firm* — Oblon, Spivak, McClelland, Maier & Neustadt, L.L.P.

(57) ABSTRACT

Multiresolution decomposition of image data before scan conversion processing is hierarchically performed, low-frequency decomposed image data and high-frequency decomposed image data with first to n-th levels are acquired, nonlinear anisotropic diffusion filtering is performed on output data from a next lower layer or the low-frequency decomposed image data in a lowest layer, and filtering for generating edge information on a signal for every layer is performed from the output data from the next lower layer or the low-frequency decomposed image data in the lowest layer. In addition, on the basis of the edge information on each layer, a signal level of the high-frequency decomposed image data is controlled for every layer and multiresolution mixing of the output data of the nonlinear anisotropic diffusion filter and the output data of the high-frequency level control, which are obtained in each layer, are hierarchically performed.

18 Claims, 7 Drawing Sheets

ULTRASONIC DIAGNOSTIC APPARATUS, ULTRASONIC IMAGE PROCESSING APPARATUS, AND ULTRASONIC IMAGE PROCESSING METHOD

CROSS-REFERENCE TO RELATED APPLICATIONS

This application is based upon and claims the benefit of priority from prior Japanese Patent Application No. 2007-338276, filed Dec. 27, 2007, the entire contents of which are incorporated herein by reference.

BACKGROUND OF THE INVENTION

1. Field of the Invention

The present invention relates to an ultrasonic diagnostic apparatus, an ultrasonic image processing apparatus, and an ultrasonic image processing method of transmitting an ultrasonic wave to the inside of a tested body and obtaining diagnostic information inside the tested body on the basis of a reflected wave from the inside of the tested body. In particular, the present invention relates to removing of a speckle included in image data.

2. Description of the Related Art

The ultrasonic diagnosis makes it possible that the pulsation of the heart or the movement of an embryo is displayed in real time by a simple operation of bringing an ultrasonic probe into contact with a body surface. In addition, since the ultrasonic diagnosis is very safe, the test may be repeatedly performed. In addition, the system size is small compared with other diagnostic apparatuses, such as an X ray, a CT, and an MRI, and a test at the bedside can also be easily performed. For this reason, it can be said that the ultrasonic diagnosis is an easy diagnostic method. An ultrasonic diagnostic apparatus used in the ultrasonic diagnosis changes in various ways with the type of a function that the ultrasonic diagnostic apparatus has. As a small ultrasonic diagnostic apparatus, an ultrasonic diagnostic apparatus that is so small as to be carried with one hand is being developed. In addition, since the ultrasonic diagnosis does not cause radioactive exposure unlike the X ray, the ultrasonic diagnosis may also be used in an obstetric treatment, a remote medical treatment, and the like. In addition, a recent ultrasonic diagnostic apparatus may collect three-dimensional biological information (volume data) by spatially scanning the inside of the tested body using an ultrasonic probe with a two-dimensional array in which ultrasonic vibrators are arrayed in a two-dimensional manner.

However, received signals from a plurality of adjacent tissues of a tested body interfere with each other due to a phase difference thereof. In addition, an image pattern differently viewed, from that in the case of mixing only amplitude information, that is, a speckle is generated. Since this speckle interferes with correctly observing the position and shape of a boundary of tissues of the tested body, various kinds of processing methods for removing the speckle have been proposed.

As one of the methods, there is a method of performing multiresolution decomposition of an object image by wavelet transform/inverse wavelet transform and performing processing for applying a threshold value, weighting, and the like to a high-frequency component of an image decomposed at each level. Although a speckle is removed in this method, there is a problem that an obtained image depends on artificial sensibility.

Accordingly, for example, JP-A-2006-116307 proposes a method of detecting an edge of an image decomposed at each level, calculating the direction of the edge for every pixel, and performing filtering for making the edge smooth in the tangential direction and the edge clear in the normal direction. Also in this case, however, there is a limitation in performance because making the edge smooth and clear is performed by a fixed filter.

On the other hand, a method of removing a speckle by a nonlinear anisotropic diffusion filter has also been proposed like 'K. Z. Abd-Elmomiem, A. M. Youssef, and Y. M. Kadah, "Real-Time Speckle Reduction and Coherence Enhancement in Ultrasound Imaging via Nonlinear Anisotropic Diffusion", IEEE transactions on biomedical engineering, vol. 49, NO. 9, Sep. 2002'. However, since the nonlinear anisotropic diffusion filter needs an operation of solving a partial differential equation for calculation, there is a problem that it takes a time for the calculation processing. In addition, although there is an effect of reducing the speckle to some extent with the single nonlinear anisotropic diffusion filter, there is also a problem that the effect is not enough.

In both of the two methods described above, an object to be processed is a two-dimensional ultrasonic image and it is premised that the process is performed after scan conversion processing in which a coordinate system of the image is converted from a transmitting and receiving system to a display system and before display. In this case, a problem occurs, for example, when only a B-mode image of an image displayed by overlapping the B-mode image and a color Doppler image each other. In addition, a recent display system has high-resolution. For this reason, many pixels should be processed for high resolution after scan conversion processing. This makes it difficult to increase the processing speed. In addition, a case in which ultrasonic image data is volume data is not specifically proposed in the known example.

BRIEF SUMMARY OF THE INVENTION

In view of the above, it is an object of the present invention to provide an ultrasonic diagnostic apparatus, an ultrasonic image processing apparatus, and an ultrasonic image processing method capable of removing a speckle of two-dimensional or three-dimensional ultrasonic image data more effectively and at high speed.

According to an aspect of the present invention, there is provided an ultrasonic diagnostic apparatus including: a data generating unit that executes transmission and reception of an ultrasonic wave in a B-mode with respect to a predetermined region of a tested body and generates ultrasonic image data; a decomposition unit that hierarchically performs multiresolution decomposition of the ultrasonic image data and acquires low-frequency decomposed image data with first to n-th levels (where, 'n' is a natural number equal to or larger than 2) and high-frequency decomposed image data with first to n-th levels; a filtering unit that performs nonlinear anisotropic diffusion filtering on output data from a next lower layer or the low-frequency decomposed image data in a lowest layer and generates edge information on a signal, for every layer, from the output data from the next lower layer or the low-frequency decomposed image data in the lowest layer; a high-frequency level control unit that controls a signal level of the high-frequency decomposed image data for every layer on the basis of the edge information of each of the layers; and a mixing unit that acquires ultrasonic image data by hierarchically performing multiresolution mixing of output data of the filtering unit and output data of the high-frequency level control unit which are obtained in each of the layers.

According to another aspect of the present invention, there is provided an ultrasonic image processing apparatus including: a decomposition unit that hierarchically performs multiresolution decomposition of ultrasonic image data, which is acquired by executing transmission and reception of an ultrasonic wave in a B-mode with respect to a predetermined region of a tested body, and acquires low-frequency decomposed image data with first to n-th levels (where, 'n' is a natural number equal to or larger than 2) and high-frequency decomposed image data with first to n-th levels; a filtering unit that performs nonlinear anisotropic diffusion filtering on output data from a next lower layer or the low-frequency decomposed image data in a lowest layer and generates edge information on a signal, for every layer, from the output data from the next lower layer or the low-frequency decomposed image data in the lowest layer; a high-frequency level control unit that controls a signal level of the high-frequency decomposed image data for every layer on the basis of the edge information of each of the layers; and a mixing unit that acquires ultrasonic image data by hierarchically performing multiresolution mixing of output data of the filtering unit and output data of the high-frequency level control unit which are obtained in each of the layers.

According to yet another aspect of the present invention, there is provided an ultrasonic image processing method including: hierarchically performing multiresolution decomposition of ultrasonic image data acquired by executing transmission and reception of an ultrasonic wave in a B-mode with respect to a predetermined region of a tested body; acquiring low-frequency decomposed image data with first to n-th levels (where, 'n' is a natural number equal to or larger than 2) and high-frequency decomposed image data with first to n-th levels on the basis of the multiresolution decomposition; executing nonlinear anisotropic diffusion filtering on output data from a next lower layer or the low-frequency decomposed image data in a lowest layer; generating edge information on a signal, for every layer, from the output data from the next lower layer or the low-frequency decomposed image data in the lowest layer; controlling a signal level of the high-frequency decomposed image data for every layer on the basis of the edge information of each of the layers; and acquiring ultrasonic image data by hierarchically performing multiresolution mixing of output data of a filtering unit and output data of a high-frequency level control unit which are obtained in each of the layers.

DETAILED DESCRIPTION OF THE INVENTION

Figure 1:
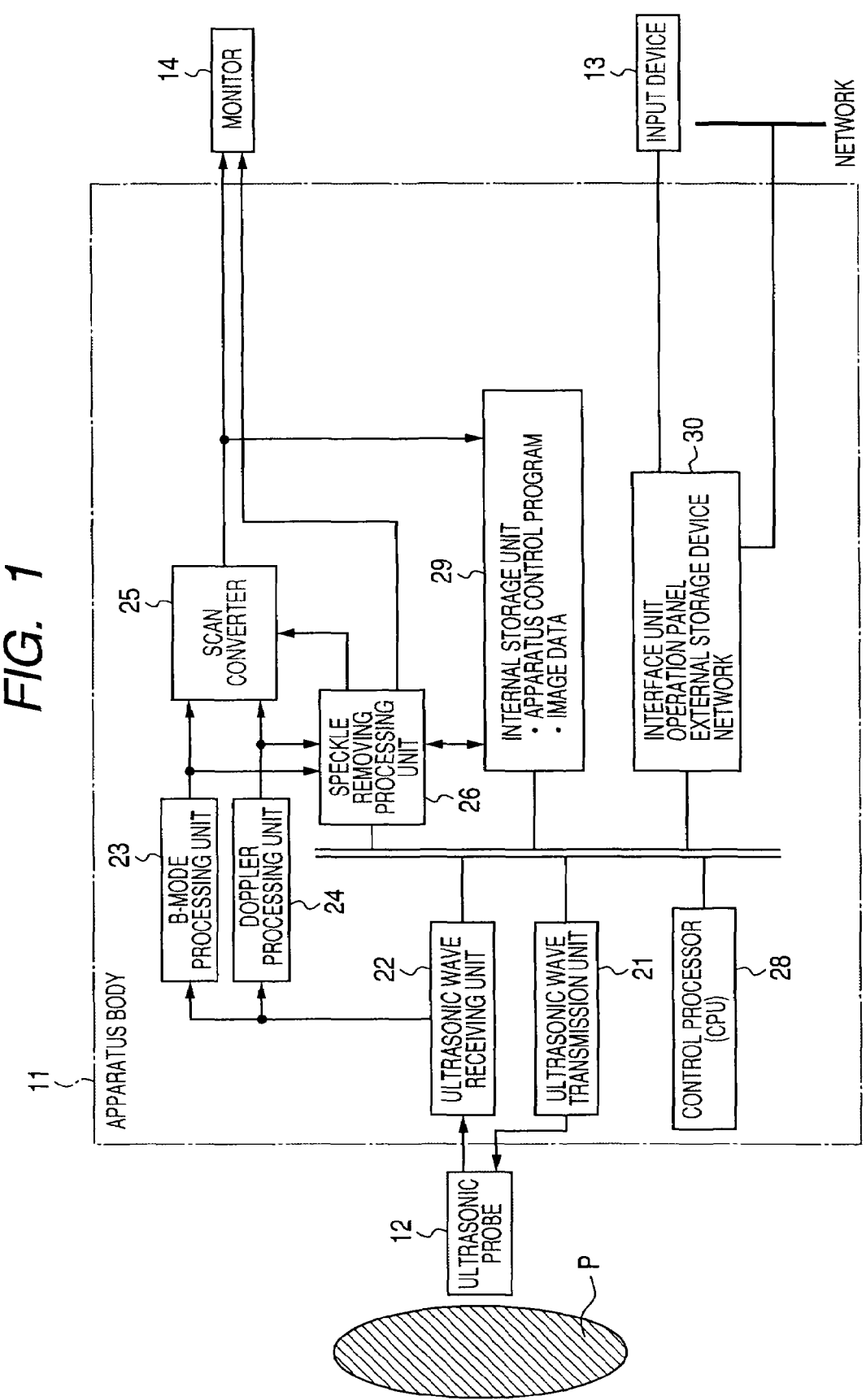
FIG. 1 is a block diagram illustrating the configuration of an ultrasonic diagnostic apparatus 1 according to a first embodiment.

Hereinafter, first to third embodiments of the present invention will be described with reference to the accompanying drawings. Moreover, in the following description, components having approximately the same function and configuration are denoted by the same reference numeral, and a repeated explanation will only be made as needed.

First Embodiment

An embodiment of the present invention will now be described with reference to the accompanying drawings. Moreover, in the following description, components having approximately the same function and configuration are denoted by the same reference numeral, and a repeated explanation will only be made as needed.

FIG. 1 is a block diagram illustrating the configuration of an ultrasonic diagnostic apparatus 1 according to the present embodiment. As shown in the drawing, an ultrasonic diagnostic apparatus 1 includes an ultrasonic probe 12, an input device 13, a monitor 14, an ultrasonic wave transmission unit 21, an ultrasonic wave receiving unit 22, a B-mode processing unit 23, a Doppler processing unit 24, a scan converter 25, a speckle removing processing unit 26, a control processor (CPU) 28, an internal storage unit 29, and an interface unit 30. Hereinafter, functions of the constituent components will be described.

The ultrasonic probe 12 generates an ultrasonic wave on the basis of a driving signal from the ultrasonic wave transmission unit 21 and has a plurality of piezoelectric vibrators that convert a reflected wave from a tested body into an electric signal, a matching layer provided in the piezoelectric vibrators, a packing material that prevents propagation of an ultrasonic wave rearward from the piezoelectric vibrators, and the like. When ultrasonic waves are transmitted from the ultrasonic probe 12 to a tested body P, the transmitted ultrasonic waves are sequentially reflected on a discontinuous surface of acoustic impedances of body tissues and are then received as an echo signal by the ultrasonic probe 12. The amplitude of the echo signal depends on a difference of acoustic impedances on the discontinuous surfaces on which the ultrasonic waves are reflected. In addition, an echo when transmitted ultrasonic waves are reflected from a moving blood flow, a heart wall, and the like is frequency shifted depending on a speed component of a moving body in the ultrasonic wave transmission direction by the Doppler effect.

The input device 13 is connected to an apparatus body 11 and has various switches, buttons, a track ball 13s, a mouse 13c, a keyboard 13d, and the like used to perform various kinds of instructions from an operator, an instruction for setting a condition or a region of interest (ROI), an instruction for setting various image quality conditions, and the like on the apparatus body 11. For example, when a user operates a stop button or a FREEZE button of the input device 13, transmission and reception of an ultrasonic wave are stopped and the ultrasonic diagnostic apparatus is temporarily stopped.

The monitor 14 displays morphological information or blood flow information in a living body on the basis of a video signal from the scan converter 25.

The ultrasonic wave transmission unit 21 has a trigger generating circuit, a delay circuit, and a pulse circuit which are not shown. The pulse circuit repeatedly generates a rate pulse for forming a transmitted ultrasonic wave at a predetermined rate frequency fr Hz (period; 1/fr second). In addition, the delay circuit makes ultrasonic waves converge in the beam shape for every channel and gives a delay time, which is required for determining transmission directivity, to each rate pulse. The trigger generating circuit applies a driving pulse to the probe 12 at the timing based on the rate pulse.

In addition, the ultrasonic wave transmission unit 21 has a function of changing a transmission frequency, a transmitted driving voltage, and the like instantaneously in order to execute a predetermined scan sequence according to the instruction of the control processor 28. In particular, the change of the transmitted driving voltage is realized by a linear amplifier type signal transmission circuit capable of changing the value instantaneously or a mechanism which performs switching of a plurality of power supply units.

The ultrasonic wave receiving unit 22 has an amplifying circuit, an A/D converter, an adder, and the like which are not shown. The amplifying circuit amplifies an echo signal received through the probe 12 for every channel. The A/D converter gives a delay time, which is required to determine the receiving directivity, to the amplified echo signal, and then the adder performs adding processing. By this addition, a reflected component from a direction according to the receiving directivity of echo signals is emphasized and overall beams in ultrasonic transmission and reception are formed by the receiving directivity and the transmission directivity.

The B-mode processing unit 23 receives an echo signal from the ultrasonic wave receiving unit 22, performs logarithmic amplification and envelope detection processing, and generates data in which the signal strength is expressed as brightness. This data is transmitted to the scan converter 25 and is displayed on the monitor 14 as a B-mode image which expresses the strength of a reflected wave with the brightness.

The Doppler processing unit 24 makes a frequency analysis of speed information from the echo signal received from the ultrasonic wave receiving unit 22, extracts a blood flow or a tissue and a contrast echo component due to the Doppler effect, and calculates blood flow information, such as an average speed, diffusion, and power, with respect to multiple points. The acquired blood flow information is transmitted to the scan converter 25 to be color-displayed on the monitor 14 as an average speed image, a diffusion image, a power image, and a combination image thereof.

The scan converter 25 mixes a scanning line signal row of ultrasonic scan with character information, scale, and the like of various parameters of data received from the B-mode processing unit 23, the Doppler processing unit 24, and the speckle removing processing unit 26, converts the result into a scanning line signal row in a typical video format represented by a television, and generates an ultrasonic diagnostic image as a display image. The scan converter 25 has a storage memory in which image data is stored, for example, so that an operator can call an image recorded in a test after diagnosis. In addition, data before being input to the scan converter 25 is a group of amplitude values or brightness values for every spatial position and is called 'raw data'.

The speckle removing processing unit 26 executes processing according to a speckle removing function, which will be described later, on the basis of the control from the control processor 28 using the raw data before scan conversion.

The control processor 28 has a function as an information processing device (computer), and is a control unit that controls an operation of the ultrasonic diagnostic apparatus body. The control processor 28 reads from the internal storage unit 29 a control program for executing image generation, image display, and the like, loads the control program onto the memory that the control processor 28 has, and executes calculation, control, and the like on various kinds of processing.

The internal storage unit 29 stores a control program for realizing image generation and display processing and scan sequence to be described later, diagnostic information (for example, a patient ID and doctor's opinion), a diagnostic protocol, transmission and reception conditions, and a program for realizing the speckle removing function, a body mark generating program, and other data groups. Moreover, the internal storage unit 29 may also be used to store an image in the image memory 26 as needed. The data in the internal storage unit 29 may also be transmitted to an external peripheral device through the interface circuit 30.

The interface unit 30 is an interface related to the input device 13, a network, and a new external storage device (not shown). Data or an analysis result of an ultrasonic image obtained by the apparatus may be transmitted to other apparatuses through the network by the interface unit 30.

(Speckle Removing Function)

Next, a speckle removing function that the ultrasonic diagnostic apparatus 1 has will be described.

This function is hierarchically performing multiresolution decomposition of image data (raw data) before scan conversion processing, acquiring low-frequency decomposed image data with first to n-th levels (where, 'n' is a natural number equal to or larger than 2) and high-frequency decomposed image data with first to n-th levels, performing nonlinear anisotropic diffusion filtering on output data from a next lower layer or the low-frequency decomposed image data in a lowest layer, and performing filtering for generating edge information on a signal, for every layer, from the output data from the next lower layer or the low-frequency decomposed image data in the lowest layer. In addition, by controlling a signal level of the high-frequency decomposed image data for every layer on the basis of the edge information on each layer and hierarchically performing multiresolution mixing of the output data of the nonlinear anisotropic diffusion filter and the output data of the high-frequency level control, which are obtained in each layer, speckle removal is performed by the synergetic effect of the multiresolution decomposition and the nonlinear anisotropic diffusion filtering. Furthermore, in the present embodiment, a case in which the number n of levels of multiresolution decomposition is 3 is exemplified for a specific explanation. However, the number n is not limited to the above example and may be any value as long as the number n is a natural number equal to or larger than 2, for example.

Figure 2:
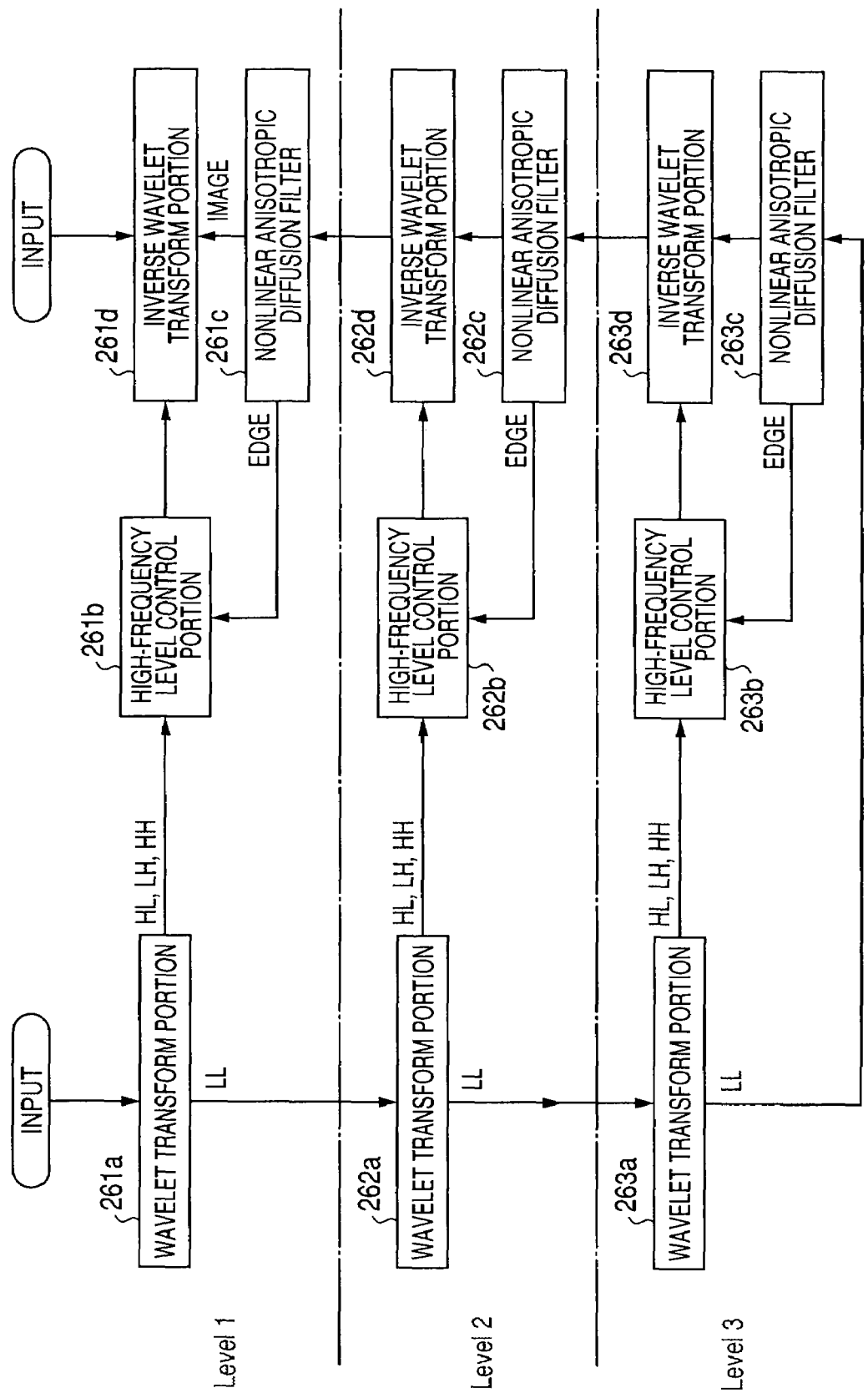
FIG. 2 is a view illustrating the flow of speckle removing processing executed in a speckle removing unit 26.

FIG. 2 is a view illustrating the flow of processing (speckle removing processing) according to the speckle removing function, which is executed in the speckle removing processing unit 26. As shown in the drawing, first, a wavelet transform portion 261*a* of level 1 performs multiresolution decomposition of image data (raw data) input from the B-mode processing unit 23. In addition, the 'wavelet transform' herein means discrete wavelet transform. In addition, the wavelet transform is only an illustration for multiresolution decomposition, and the technical spirit of the present invention is not limited to the above method. For example, the multiresolution decomposition may also be realized by other methods, such as the Laplacian pyramid method. As a result of the multiresolution decomposition, image data after decomposition is decomposed into a low-frequency image LL, a horizontal and high-frequency image LH, a vertical and high-frequency image HL, and a diagonal and high-frequency image HH, of which horizontal and vertical lengths are half of those before the decomposition. Among the decomposed image data, the low-frequency image LL is output to a wavelet transform portion 262a of level 2 and the horizontal and high-frequency image LH, the vertical and high-frequency image HL, and the diagonal and high-frequency image HH are output to a high-frequency level control portion 261b.

In addition, the wavelet transform portion 262a of level 2 acquires the low-frequency image LL, the horizontal and high-frequency image LH, the vertical and high-frequency image HL, and the diagonal and high-frequency image HH by performing multiresolution decomposition of the low-frequency image LL input from the wavelet transform portion 261a of level 1, and outputs the low-frequency image LL to a wavelet transform portion 263a of level 2 and outputs the horizontal and high-frequency image LH, the vertical and high-frequency image HL, and the diagonal and high-frequency image HH to a high-frequency level control portion 262b.

In addition, the wavelet transform portion 263a of level 2 acquires the low-frequency image LL, the horizontal and high-frequency image LH, the vertical and high-frequency image HL, and the diagonal and high-frequency image HH by performing multiresolution decomposition of the low-frequency image LL input from the wavelet transform portion 262a of level 2, and outputs the low-frequency image LL to a nonlinear anisotropic diffusion filter 263c of level 3 and outputs the horizontal and high-frequency image LH, the vertical and high-frequency image HL, and the diagonal and high-frequency image HH to a high-frequency level control portion 263b.

Then, a nonlinear anisotropic diffusion filter 263c of level 3 performs filtering of the low-frequency image LL and outputs the low-frequency image LL after the filtering to an inverse wavelet transform portion 263d. In addition, a nonlinear anisotropic diffusion filter 263c of level 3 generates edge information based on the low-frequency image LL and outputs the edge information to the inverse wavelet transform portion 263b.

Here, a nonlinear anisotropic diffusion filter will be described. The nonlinear anisotropic diffusion filter is expressed by the following partial differential equation (1).

$$\frac{\partial I}{\partial T} = div[D\nabla I]$$ [Expression 1]

'I' indicates a pixel level of an image to be processed, '∇I' indicates the gradient vector, and 't' indicates a time taken for processing. 'D' indicates diffusion tensor and may be expressed by the following expression (2).

$$D = \begin{pmatrix} d_{11} & d_{12} \\ d_{12} & d_{22} \end{pmatrix} = R\begin{pmatrix} \lambda_1 & 0 \\ 0 & \lambda_2 \end{pmatrix}R^T$$ [Expression 2]

'R' indicates a rotation matrix, and the diffusion tensor D indicates an operation of applying coefficients $\lambda_1$ and $\lambda_2$ to the gradient vector of each pixel in a specific direction and a direction perpendicular to the specific direction. The direction is a direction of the edge of a detected image, and the coefficient depends on the size of the edge.

In order to detect the size and direction of the edge, it is general to acquire the structure tensor of the image and to calculate an eigenvalue. The eigenvalue is related with the size of the edge, and the eigenvector indicates the direction of the edge. The structure tensor is defined as the following expression (3).

$$S = G_\rho * \begin{pmatrix} I_x^2 & I_xI_y \\ I_xI_y & I_y^2 \end{pmatrix}$$ [Expression 3]

$$= \begin{pmatrix} G_\rho * I_x^2 & G_\rho * (I_xI_y) \\ G_\rho * (I_xI_y) & G_\rho * I_y^2 \end{pmatrix}$$

$$= \begin{pmatrix} s_{11} & s_{12} \\ s_{12} & s_{22} \end{pmatrix}$$

Here, '$I_x$' and '$I_y$' indicate spatial differentiation of the image I to be processed in x (horizontal) and y (vertical) directions thereof, 'Gp' indicates a two-dimensional Gaussian function, and an operator '*' indicates convolution. Calculation of the size and direction of an edge may not be necessarily performed according to the above method. Instead of calculating $I_x$ and $I_y$ as a first step of processing, a sobel filter or a high-frequency component of multiresolution decomposition may also be applied.

Although a method of calculating the coefficients $\lambda_1$ and $\lambda_2$ changes with characteristics of an ultrasonic image in each diagnostic field, it is useful to prepare a general expression so that the coefficients can be adjusted by some parameters.

In addition, calculation of the filter itself is performed in a numeric analysis method of a partial differential equation. That is, from a pixel level of a pixel at a predetermined point and pixel levels of, for example, nine pixels around the pixel and each element value of diffusion tensor at time t, a new pixel level at the point is calculated at time t+Δt. Then, the same calculation is repeated once to several times with t+Δt as new t.

Figure 3:
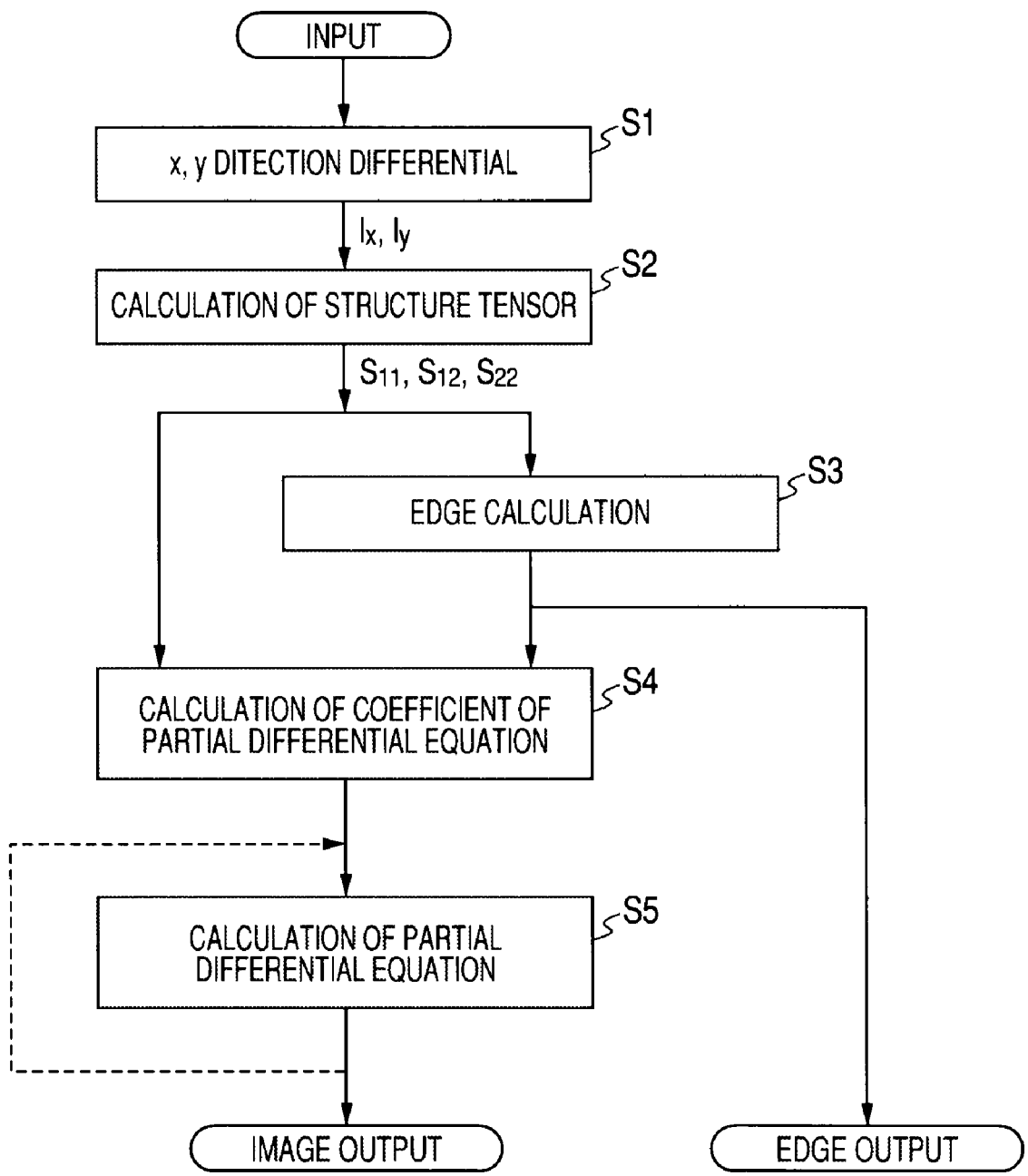
FIG. 3 is a flow chart illustrating the procedure of filtering processing of a nonlinear anisotropic diffusion filter 263c (or 261c, 262c)

FIG. 3 is a flow chart illustrating the procedure of filtering processing of the nonlinear anisotropic diffusion filter 263c (or 261c or 262c). As shown in the drawing, the nonlinear anisotropic diffusion filter 263c differentiates the input low-frequency image LL in the x and y directions (step S1) and calculates the structure tensor $s_{11}$, $s_{12}$, and $s_{22}$ (step S2). In addition, calculation of the Gaussian filter is also included in the calculation of step S2.

Then, the nonlinear anisotropic diffusion filter 263c calculates the size of the edge from each element of the structure tensor (step S3). This calculation result is used for partial differential equation calculation in a subsequent stage and processing in the high-frequency level control portion 263b (or 262b or 261b).

Then, the nonlinear anisotropic diffusion filter 263c calculates each coefficient used in the numerical analysis of the partial differential equation of the nonlinear anisotropic diffusion filter on the basis of each element of the structure tensor (step S4). In addition, in this step, calculation of the structure tensor is also included, and the size of the edge is also used in the calculation for efficient processing.

Then, the nonlinear anisotropic diffusion filter 263c executes numeric-analysis calculation of the partial differential equation once or several times repeatedly (step S5). The result obtained by the calculation is output to the inverse wavelet transform portion 263d (or 261d or 262d).

Then, as shown in FIG. 2, the high-frequency level control portion 263b of level 3 is input with the horizontal and high-frequency image LH, the vertical and high-frequency image HL, the diagonal and high-frequency image HH, and edge information on these three components and controls a high-frequency level according to the images and the edge information. In addition, in the present embodiment, the edge information is the size of an edge standardized on the basis of the eigenvalue of the structure tensor, a product of the size and each high-frequency image is taken for every pixel, and a control coefficient of each high-frequency image is applied to the result. As another example, there is a method of setting a threshold value for the size of an edge, determining the size of an edge equal to or larger than the threshold value as an edge, and applying a control coefficient of each high-frequency image to a region other than the edge. Three high-frequency images processed as described above are input to the inverse wavelet transform portion 263d.

The inverse wavelet transform portion 263d forms one composite image from the low-frequency image LL output from the nonlinear anisotropic diffusion filter 263c and the horizontal and high-frequency image LH, the vertical and high-frequency image HL, and the diagonal and high-frequency image HH output from the high-frequency level control portion 263b. The horizontal and vertical lengths of the composite image are twice those of an input image.

The composite image output from the inverse wavelet transform portion 263d of level 3 is input to the nonlinear anisotropic diffusion filter 262c of level 2, is subjected to the same filtering processing as the level 3, and is then transmitted to a low-frequency image input of the inverse wavelet transform portion 262d. On the other hand, the horizontal and high-frequency image LH, the vertical and high-frequency image HL, and the diagonal and high-frequency image HH output from the wavelet transform portion 262a are subjected to the same high-frequency level control as the level 3 in the high-frequency level control portion 262b and are transmitted to a high-frequency image input of the inverse wavelet transform portion 262d. The inverse wavelet transform portion 262d forms a composite image data from one low-frequency image and three high-frequency images in the same manner as the level 3.

In addition, the composite image output from the inverse wavelet transform portion 262d of level 2 is input to the nonlinear anisotropic diffusion filter 261c of level 1, is subjected to the same filtering processing as the levels 2 and 3, and is then transmitted to a low-frequency image input of the inverse wavelet transform portion 261d. On the other hand, the horizontal and high-frequency image LH, the vertical and high-frequency image HL, and the diagonal and high-frequency image HH output from the wavelet transform portion 261a are subjected to the same high-frequency level control as the levels 2 and 3 in the high-frequency level control portion 261b and are transmitted to a high-frequency image input of the inverse wavelet transform portion 261d. The inverse wavelet transform portion 261d forms a composite image from one low-frequency image and three high-frequency images in the same manner as the levels 2 and 3.

The composite image data formed by the above-described processing is transmitted from the speckle removing processing unit 26 to the scan converter 25. The scan converter 25 mixes the composite image data with character information, scale, and the like of various parameters, converts the result into a scanning line signal row in a normal video format represented as a television, and generates an ultrasonic diagnostic image as a display image. The generated ultrasonic image is expressed in a predetermined form on the monitor 14.

(Effects)

According to the configuration described above, the following effects can be obtained. According to the ultrasonic diagnostic apparatus, multiresolution decomposition of image data (raw data) before scan conversion processing is hierarchically performed, low-frequency decomposed image data with first to n-th levels (where, 'n' is a natural number equal to or larger than 2) and high-frequency decomposed image data with first to n-th levels are acquired, nonlinear anisotropic diffusion filtering is performed on output data from a next lower layer or the low-frequency decomposed image data in the lowest layer, and filtering for generating edge information on a signal for every layer is performed from the output data from the next lower layer or the low-frequency decomposed image data in the lowest layer. In addition, by controlling a signal level of the high-frequency decomposed image data for every layer on the basis of the edge information on each layer and hierarchically performing multiresolution mixing of the output data of the nonlinear anisotropic diffusion filter and the output data of the high-frequency level control, which are obtained in each layer, speckle removal is performed by the synergetic effect of the multiresolution decomposition and the nonlinear anisotropic diffusion filtering. Therefore, compared with a case in which only a filter is applied, speckle removing processing in which the speckle is fine and an interface of tissues is clearer can be realized. As a result, a high-quality diagnostic image can be provided, which can contribute to improving the quality of image diagnosis.

In addition, according to the ultrasonic diagnostic apparatus, the nonlinear anisotropic diffusion filter is applied after reducing an image by multiresolution decomposition. Accordingly, compared with a case where a nonlinear anisotropic diffusion filter is applied directly to an original image, the processing area (amount of data to be processed) can be reduced. As a result, high-speed processing can be realized compared with a nonlinear anisotropic diffusion filter which requires a time for calculation.

Furthermore, according to the ultrasonic diagnostic apparatus, since only a B-mode image is processed in the speckle removing processing, the processing does not affect a color Doppler image even if the color Doppler image overlaps the B-mode image. As a result, high-quality speckle removal can be realized without restricting the degree of freedom in image processing or image display and without affecting the processing speed even if the resolution of a display system is increased.

Second Embodiment

In the first embodiment, an example in which speckle removing processing is executed on two-dimensional image data (raw data) has been illustrated. On the other hand, in the present embodiment, a case in which an ultrasonic diagnostic apparatus 1 executes speckle removing processing on three-dimensional volume data (raw data) will be described.

Figure 4:
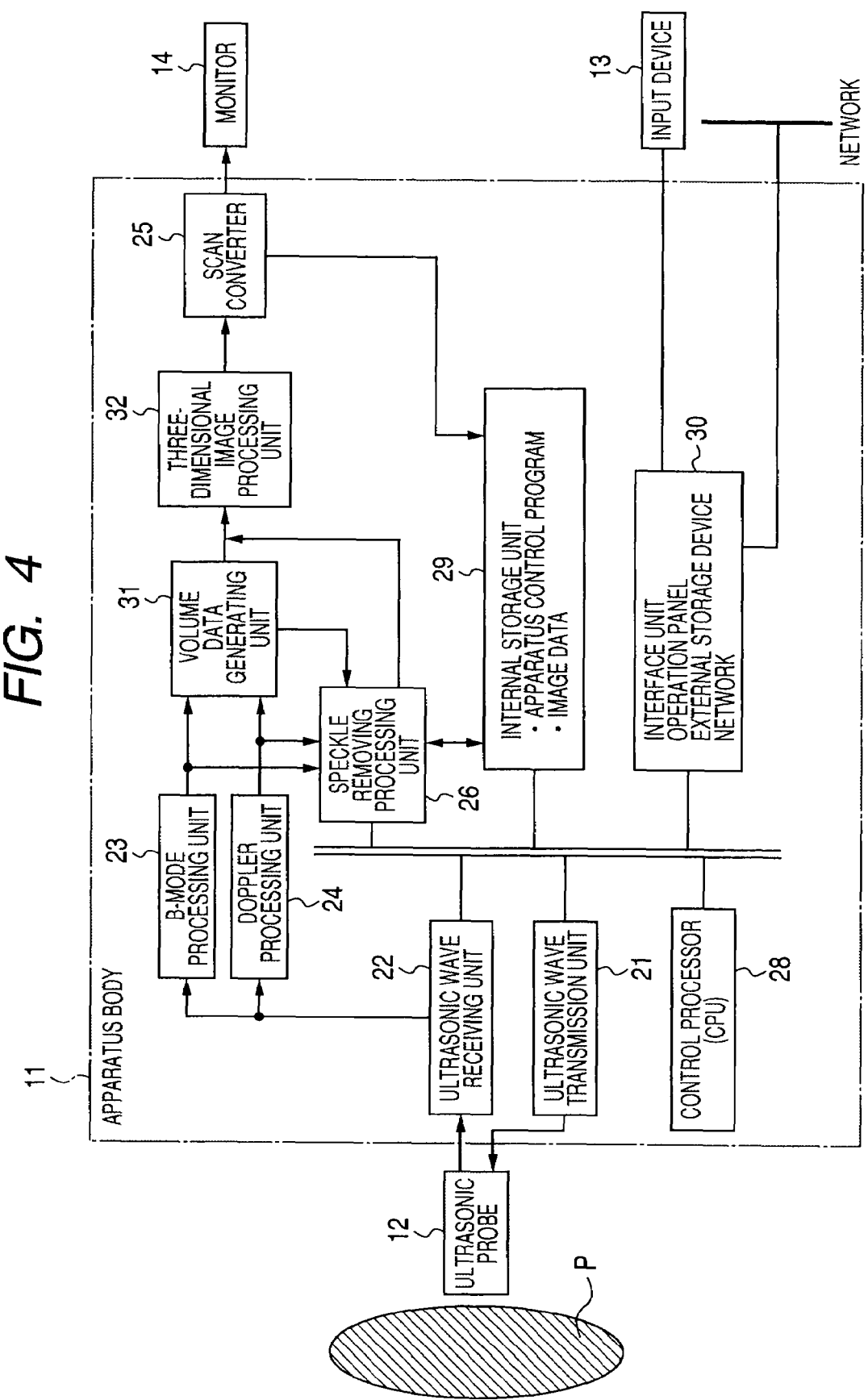
FIG. 4 is a view illustrating the configuration of an ultrasonic diagnostic apparatus 1 according to a second embodiment.

FIG. 4 is a view illustrating the configuration of the ultrasonic diagnostic apparatus 1 according to the present embodiment. The configuration shown in FIG. 4 is different from that shown in FIG. 1 in that a volume data generating unit 31 is further provided and a speckle removing processing unit 26 performs speckle removing processing on volume data from the volume data generating unit 31.

The volume data generating unit 31 generates B-mode volume data using B-mode image data received from a B-mode processing unit 23. In addition, the volume data generating unit 31 generates Doppler-mode image volume data using Doppler-mode data received from a Doppler processing unit 24.

A three-dimensional image processing unit 32 performs predetermined image processing, such as volume rendering, multi planar reconstruction (MPR), and maximum intensity projection (MIP), on the volume data received from the volume data generating unit 31 or the B-mode volume data which is received from the speckle removing processing unit 26 and has been subjected to speckle removing processing.

Figure 5A:
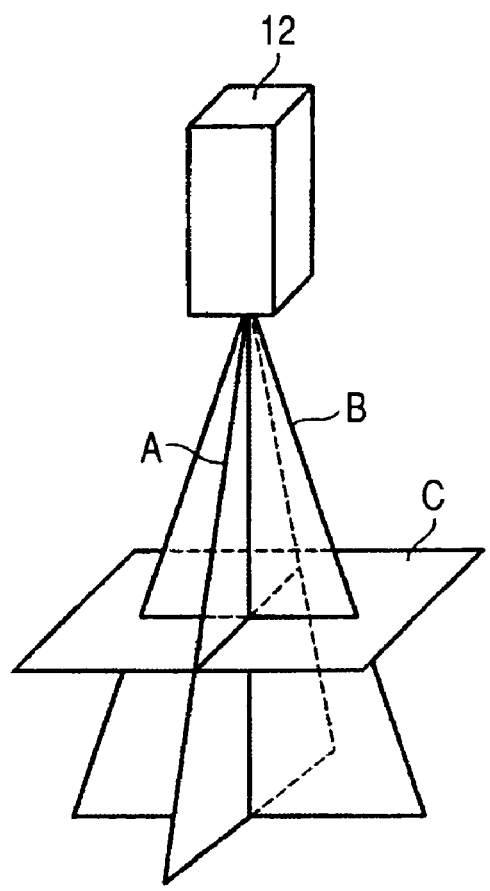
FIGS. 5A and 5B are views for explaining a speckle removing function in the second embodiment.
Figure 5B:
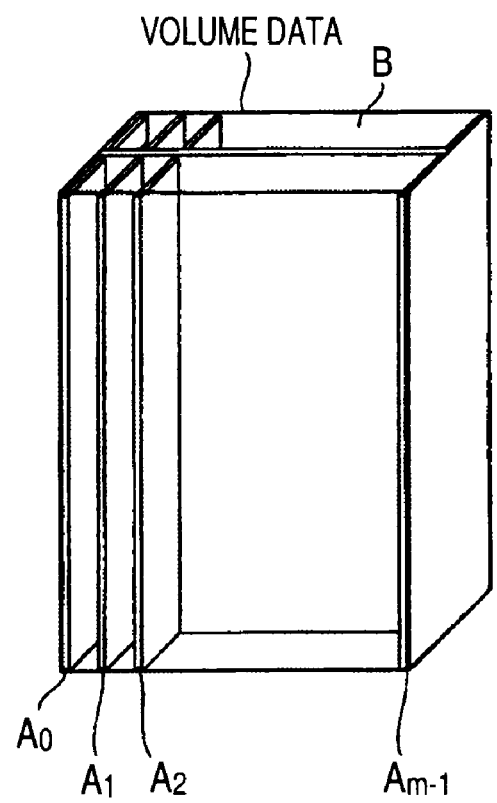

FIGS. 5A and 5B are views for explaining a speckle removing function in the present embodiment. As shown in FIGS. 5A and 5B, among cross sections volume data, two faces which cross a central axis of an object region (ultrasonic scan region) of ultrasonic scan executed by using the ultrasonic probe 12 and which are perpendicular to each other are defined as A face and B face, and a face perpendicular to the central axis and the A and B faces is defined as a C face.

The B-mode volume data received from the volume data generating unit 31 may be assumed to be a group (that is, a group of two-dimensional image data parallel to the A face) of 'm' planes A0, A1, . . . Am−1 parallel to the A face. The speckle removing processing unit 26 executes speckle removing processing on the B-mode volume data by performing the speckle removing processing described in the first embodiment on all two-dimensional image data parallel to the A face.

The three-dimensional image processing unit 32 receives the B-mode volume data subjected to the speckle removing processing from the speckle removing processing unit 26 and the Doppler volume data from the volume data generating unit 31 and executes image processing, such as volume rendering, on the basis of the B-mode volume data and the Doppler volume data. Three-dimensional image data generated by the image processing is converted into a scanning line signal row in a normal video format by the scan converter 25 and is displayed in a predetermined form on the monitor 14.

In the ultrasonic diagnostic apparatus according to the present embodiment, the speckle removing processing can be executed on the entire B-mode volume data by performing the speckle removing processing on all of the two-dimensional image data that forms the B-mode volume data. As a result, an ultrasonic image from which speckle is removed can be acquired not only on the A face but about the B and C faces. Particularly on the C face which is required to be smooth, the speckle is fine and an interface of tissues becomes clearer. Accordingly, effective speckle removal can be realized in the entire three-dimensional space.

Third Embodiment

As described above, in the second embodiment, an example in which the present invention is applied to the three-dimensional volume data before three-dimensional image processing has been illustrated. However, in a third embodiment, an example in which the present invention is applied to a three-dimensional display after three-dimensional image processing will now be illustrated.

In the second embodiment, an example in which speckle removing processing is executed on B-mode volume data before three-dimensional image processing has been illustrated. On the other hand, in the present embodiment, a case in which an ultrasonic diagnostic apparatus 1 executes speckle removing processing on image data after three-dimensional image processing will be described.

Figure 6:
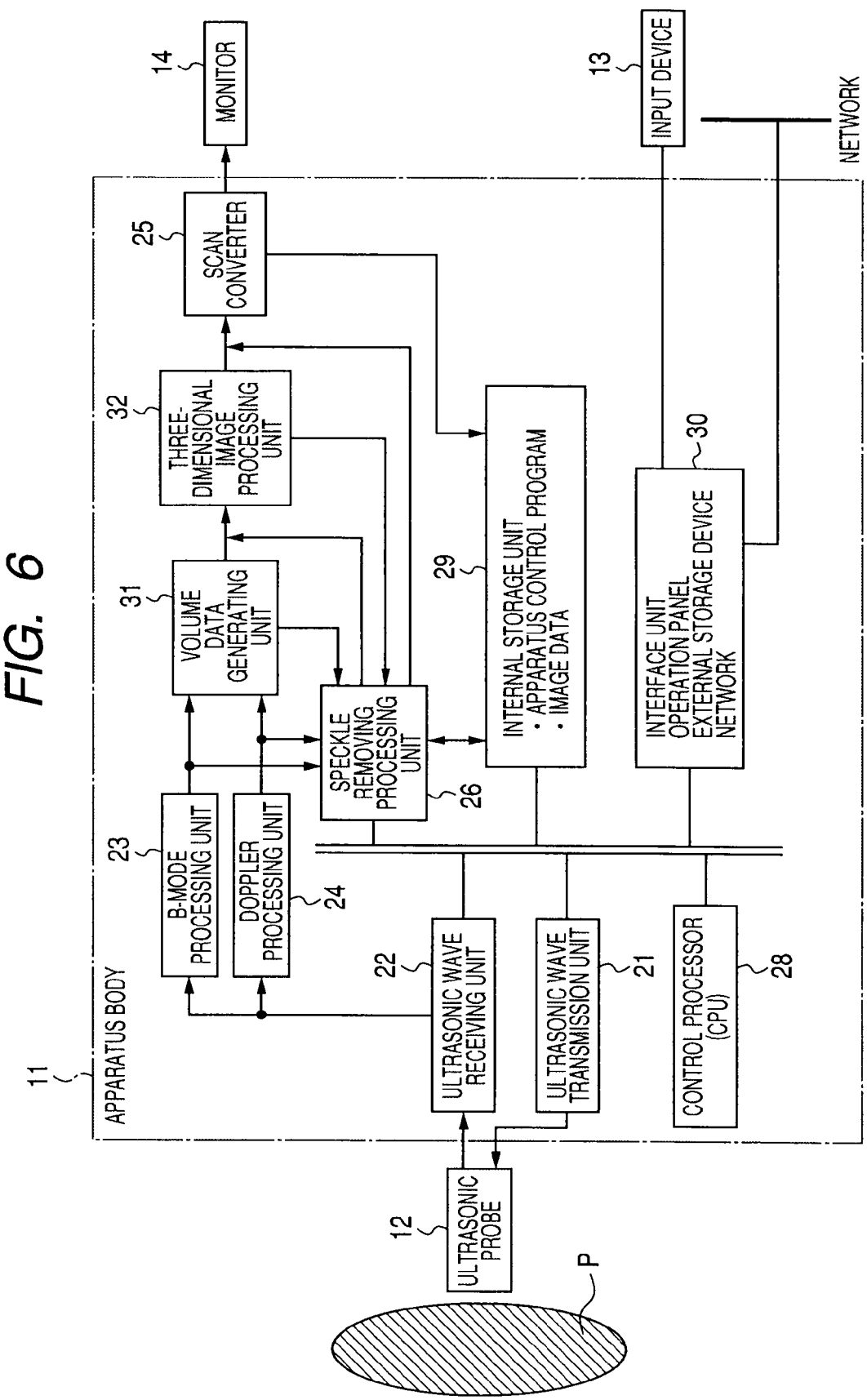
FIG. 6 is a view illustrating the configuration of an ultrasonic diagnostic apparatus 1 according to a third embodiment.

FIG. 6 is a view illustrating the configuration of the ultrasonic diagnostic apparatus 1 according to the present embodiment. The configuration shown in FIG. 6 is different from that shown in FIG. 4 in that a volume data generating unit 31 is further provided and a speckle removing processing unit 26 performs speckle removing processing on image data from a three-dimensional image processing unit 32.

Figure 7:
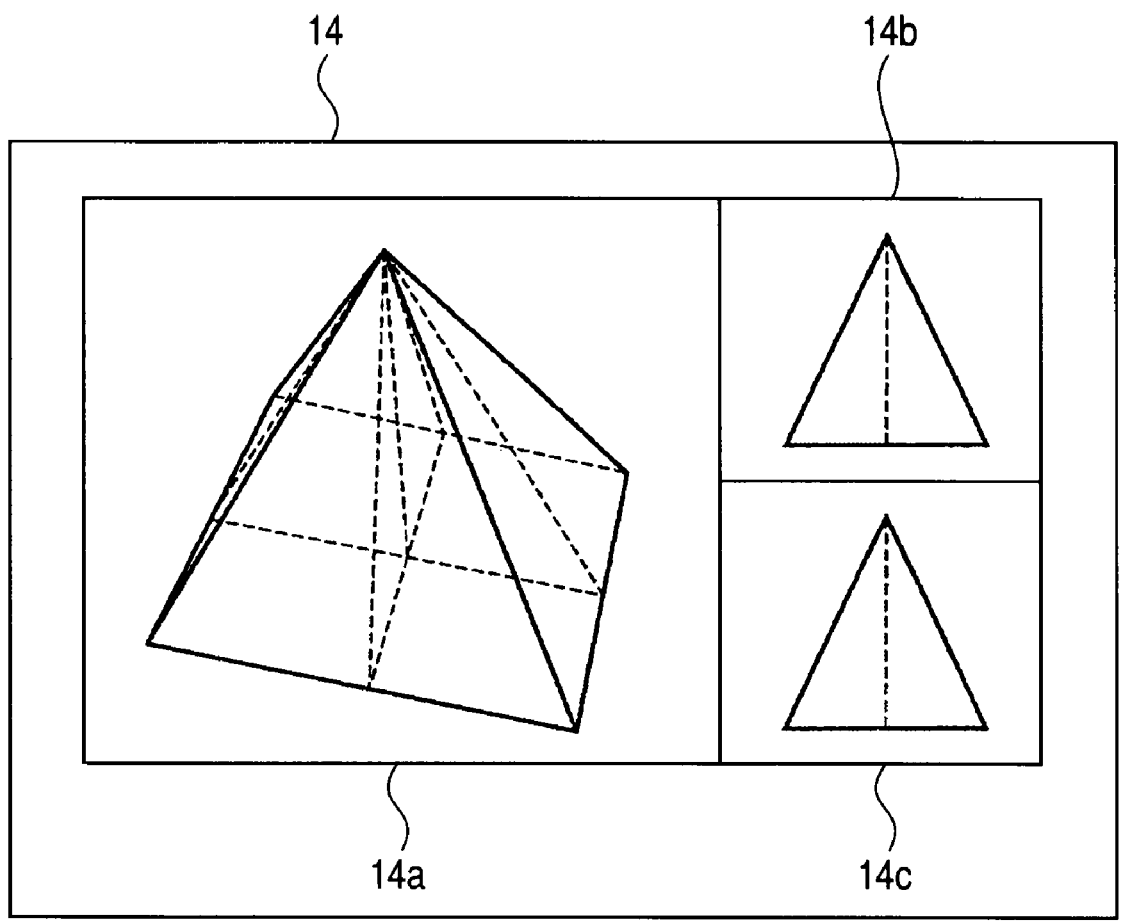
FIG. 7 is a view illustrating an example in which a plurality of three-dimensional images (a volume rendering image 14a, a first multi planar reconstruction image 14b, and a second multi planar reconstruction image 14c) are displayed simultaneously on a monitor.

FIG. 7 is a view illustrating an example in which a plurality of three-dimensional images (a volume rendering image 14*a*, a first multi planar reconstruction image 14*b*, and a second multi planar reconstruction image 14*c*) are displayed simultaneously on the monitor 14.

The speckle removing processing unit 26 executes, for example, the speckle removing processing, which was described in the first embodiment, on three-dimensional image data received from the three-dimensional image processing unit 32. In this case, for example, when a display form shown in FIG. 7 is adopted, the speckle removing processing may be performed on at least one of the volume rendering image 14*a*, the first multi planar reconstruction image 14*b*, and the second multi planar reconstruction image 14*c*. In addition, it is needless to say that the three-dimensional image data received from the three-dimensional image processing unit 32 be not limited to examples of the volume rendering image 14*a*, the first multi planar reconstruction image 14*b*, and the second multi planar reconstruction image 14*c*. For example, the speckle removing processing may also be executed on three-dimensional image data obtained by other rendering and reconstruction processing, such as surface rendering and maximum intensity projection.

In addition, the present invention is not limited to the embodiments described above but may be embodied in practice by modifying constituent components without departing from the scope and spirit of the present invention. For example, specific modifications include the following examples.

(1) Each of the functions in the present embodiment may be realized by installing a program, which is used to execute corresponding processing, in a computer, such as a workstation, and then loading the program onto a memory.

In this case, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

(2) In the second embodiment described above, a surface crossing the central axis of an ultrasonic scan region is set as a cross section on which the speckle removing processing is performed. However, the speckle removing processing may be performed on an arbitrary cross section of a three-dimensional space without being limited to the example.

In addition, various kinds of inventions may be realized by proper combination of the plurality of constituent components disclosed in the embodiments described above. For example, some constituent components may be eliminated from all components shown in the above embodiments. Moreover, constituent components in different embodiments may be appropriately combined.

What is claimed is:
1. An ultrasonic diagnostic apparatus comprising:
    a data generating unit that executes transmission and reception of an ultrasonic wave in a B-mode with respect to a predetermined region of a tested body and generates ultrasonic image data;

a decomposition unit that hierarchically performs multiresolution decomposition of the ultrasonic image data and acquires low-frequency decomposed image data with first to n-th levels (where, 'n' is a natural number equal to or larger than 2) and high-frequency decomposed image data with first to n-th levels;

a filtering unit that performs nonlinear anisotropic diffusion filtering on output data from a next lower layer or the low-frequency decomposed image data in a lowest layer and generates edge information on a signal, for every layer, from the output data from the next lower layer or the low-frequency decomposed image data in the lowest layer;

a high-frequency level control unit that controls a signal level of the high-frequency decomposed image data for every layer on the basis of the edge information of each of the layers; and a mixing unit that acquires ultrasonic image data by hierarchically performing multiresolution mixing of output data of the filtering unit and output data of the high-frequency level control unit which are obtained in each of the layers.

2. The ultrasonic diagnostic apparatus according to claim 1,
wherein the multiresolution decomposition is wavelet transform, and
the multiresolution mixing is inverse wavelet transform.

3. The ultrasonic diagnostic apparatus according to claim 1,
wherein each of the multiresolution decomposition and the multiresolution mixing is a Laplacian pyramid method.

4. The ultrasonic diagnostic apparatus according to claim 1,
wherein the ultrasonic image data is raw data before scan conversion processing.

5. The ultrasonic diagnostic apparatus according to claim 1,
wherein the ultrasonic image data is volume data, and
the decomposition unit executes the multiresolution decomposition on each of a plurality of two-dimensional ultrasonic image data that forms the volume data.

6. The ultrasonic diagnostic apparatus according to claim 1,
wherein the ultrasonic image data is volume data, and
the decomposition unit executes the multiresolution decomposition on each of a plurality of three-dimensional ultrasonic image data generated by using the volume data.

7. An ultrasonic image processing apparatus comprising:
a decomposition unit that hierarchically performs multiresolution decomposition of ultrasonic image data, which is acquired by executing transmission and reception of an ultrasonic wave in a B-mode with respect to a predetermined region of a tested body, and acquires low-frequency decomposed image data with first to n-th levels (where, 'n' is a natural number equal to or larger than 2) and high-frequency decomposed image data with first to n-th levels;

a filtering unit that performs nonlinear anisotropic diffusion filtering on output data from a next lower layer or the low-frequency decomposed image data in a lowest layer and generates edge information on a signal, for every layer, from the output data from the next lower layer or the low-frequency decomposed image data in the lowest layer;

a high-frequency level control unit that controls a signal level of the high-frequency decomposed image data for every layer on the basis of the edge information of each of the layers; and a mixing unit that acquires ultrasonic image data by hierarchically performing multiresolution mixing of output data of the filtering unit and output data of the high-frequency level control unit which are obtained in each of the layers.

8. The ultrasonic image processing apparatus according to claim 7,
wherein the multiresolution decomposition is wavelet transform, and
the multiresolution mixing is inverse wavelet transform.

9. The ultrasonic image processing apparatus according to claim 7,
wherein each of the multiresolution decomposition and the multiresolution mixing is a Laplacian pyramid method.

10. The ultrasonic image processing apparatus according to claim 7,
wherein the ultrasonic image data is raw data before scan conversion processing.

11. The ultrasonic image processing apparatus according to claim 7,
wherein the ultrasonic image data is volume data, and
the decomposition unit executes the multiresolution decomposition on each of a plurality of two-dimensional ultrasonic image data that forms the volume data.

12. The ultrasonic image processing apparatus according to claim 7,
wherein the ultrasonic image data is volume data, and
the decomposition unit executes the multiresolution decomposition on each of a plurality of three-dimensional ultrasonic image data generated by using the volume data.

13. An ultrasonic image processing method comprising:
hierarchically performing multiresolution decomposition of ultrasonic image data acquired by executing transmission and reception of an ultrasonic wave in a B-mode with respect to a predetermined region of a tested body;
acquiring low-frequency decomposed image data with first to n-th levels (where, 'n' is a natural number equal to or larger than 2) and high-frequency decomposed image data with first to n-th levels on the basis of the multiresolution decomposition;
executing nonlinear anisotropic diffusion filtering on output data from a next lower layer or the low-frequency decomposed image data in a lowest layer;
generating edge information on a signal, for every layer, from the output data from the next lower layer or the low-frequency decomposed image data in the lowest layer;
controlling a signal level of the high-frequency decomposed image data for every layer on the basis of the edge information of each of the layers; and
acquiring ultrasonic image data by hierarchically performing multiresolution mixing of output data of a filtering unit and output data of a high-frequency level control unit which are obtained in each of the layers.

14. The ultrasonic image processing method according to claim 13,
wherein the multiresolution decomposition is wavelet transform, and
the multiresolution mixing is inverse wavelet transform.

15. The ultrasonic image processing method according to claim 13,
wherein each of the multiresolution decomposition and the multiresolution mixing is a Laplacian pyramid method.

16. The ultrasonic image processing method according to claim 13,
wherein the ultrasonic image data is raw data before scan conversion processing.

17. The ultrasonic image processing method according to claim 13,
wherein the ultrasonic image data is volume data, and
the decomposition unit executes the multiresolution decomposition on each of a plurality of two-dimensional ultrasonic image data that forms the volume data.

18. The ultrasonic image processing method according to claim 13, wherein the ultrasonic image data is volume data, and the decomposition unit executes the multiresolution decomposition on each of a plurality of three-dimensional ultrasonic image data generated by using the volume data.

* * * * *